(12) United States Patent
Lin

(10) Patent No.: US 8,992,751 B2
(45) Date of Patent: Mar. 31, 2015

(54) TEST STRIPS AND PREPARATION METHOD THEREOF

(71) Applicant: Compose Element Limited, New Taipei (TW)

(72) Inventor: Tsu-Tai Lin, New Taipei (TW)

(73) Assignee: Compose Element Limited, New Taipei (TW)

( * ) Notice: Subject to any disclaimer, the term of this patent is extended or adjusted under 35 U.S.C. 154(b) by 75 days.

(21) Appl. No.: 13/858,520

(22) Filed: Apr. 8, 2013

(65) Prior Publication Data

US 2013/0284595 A1    Oct. 31, 2013

Related U.S. Application Data

(60) Provisional application No. 61/621,673, filed on Apr. 9, 2012.

(51) Int. Cl.
  *G01N 27/327*   (2006.01)
  *C12Q 1/00*     (2006.01)
  *G01N 27/30*    (2006.01)

(52) U.S. Cl.
  CPC ............ *C12Q 1/006* (2013.01); *G01N 27/307* (2013.01); *G01N 27/3272* (2013.01)
  USPC .................................. 204/403.04; 204/403.01

(58) Field of Classification Search
  CPC ..................................... G01N 27/327–27/3274
  USPC ........................................ 204/403.01–403.15
  See application file for complete search history.

(56) References Cited

U.S. PATENT DOCUMENTS

2008/0029390 A1 *  2/2008  Roche et al. ............. 204/403.06
2009/0000947 A1 *  1/2009  Akahori et al. .......... 204/403.14

FOREIGN PATENT DOCUMENTS

WO    WO 2006/011062 A2 *  2/2006

\* cited by examiner

*Primary Examiner* — J. Christopher Ball
(74) *Attorney, Agent, or Firm* — WPAT, P.C.; Anthony King

(57) ABSTRACT

The present invention relates to test strips and preparation method thereof. More particularly, the present invention relates to a test strip comprising: (a) an insulating substrate; (b) an electrode system disposed on the insulating substrate; (c) an insulation layer disposed on the electrode system, in which an accommodation space is disposed at one side of the insulation layer for exposing a part of the electrode system to carry out an electrochemical reaction of an analyte; and (d) a gel, disposed in the accommodation space and formed by dissolving a reactive enzyme reacting with the analyte in a hydrogel and being cured.

7 Claims, 2 Drawing Sheets

TEST STRIPS AND PREPARATION METHOD THEREOF

CROSS-REFERENCE

This application is a Non-Provisional application of a related Provisional Application No. 61/621,673 filed on Apr. 9, 2012 with a title of "TEST STRIPS AND REPARATION METHOD THEREOF", all of which is hereby incorporated by reference in its entirety.

FIELD OF THE INVENTION

The present invention relates to test strips and preparation method thereof. More particularly, the present invention relates to a test strip and preparation for detecting blood sugar.

DESCRIPTION OF PRIOR ART

Diabetes, hyperuricemia and high cholesterol have been chronic diseases of modern civilization society for a long time. Recently, because production of an electrode-type detection specimen was easily produced at a low cost and because portable cheap test detectors are popular, various test detectors, such as biochemical detectors for detecting blood sugar, uric acid or cholesterol, were produced commercially available in the market.

Using diabetes patients as an example, a general diabetes patient needed to detect his blood sugar by himself to get an instant concentration of his blood sugar in order to maintain his blood sugar concentration by staying a strict diet. When the diabetes patient saw a doctor and provided the blood sugar recording data as a reference data to medical staffs after his blood sugar concentrations were detected, the diabetes patient would obtained an appropriate therapeutic treatment. Early blood sugar concentration detection was implemented by testing a urine sugar test strip, and a level of the blood sugar concentration was known by using a colorimetric method. While a current blood sugar test is finger blood collection detection, for the blood sugar detectors commercial available in the market, another current test strips are produced by using an electrochemical way. Firstly a trace amount of blood of a human body is collected, the blood is dripped onto an enzyme area on a reaction specimen to obtain a blood glucose value of the human body by analyzing by using a blood sugar detector.

A process of manufacturing an enzyme area of a conventional test strip was complicated and had many drawbacks. After an enzyme solution was dripped, a drying step was needed. It was not easy to accurately drip the enzyme solution, to drip an accurate amount and to align. A defective product would be produced under a large variation of drying conditions. Therefore, it is an object of the present to solve the problems of the well-known process of manufacturing the conventional test strip.

SUMMARY OF THE INVENTION

Figure 1:
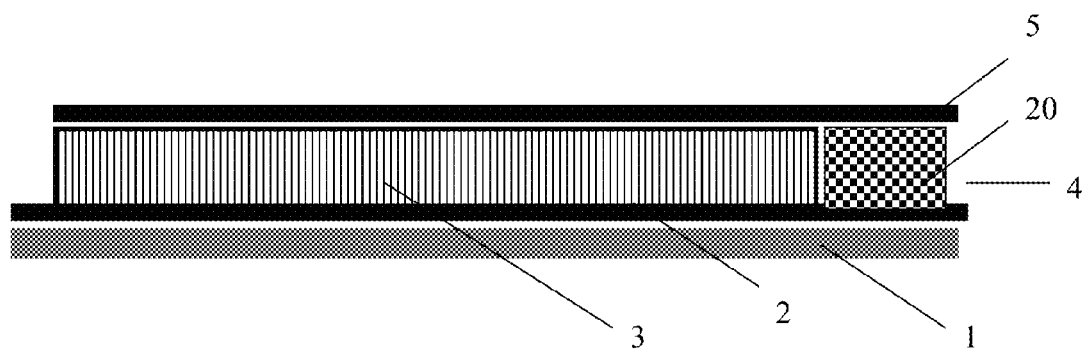
FIG. 1 is a structural schematic view of a test strip of the present invention.

The present invention firstly provides a test strip comprising:
(a) an insulating substrate;
(b) an electrode system disposed on the insulating substrate;
(c) an insulation layer disposed on the electrode system, in which an accommodation space is disposed at one side of the insulation layer for exposing a part of the electrode system to carry out an electrochemical reaction of an analyte; and
(d) a gel, disposed in the accommodation space and formed by dissolving a reactive enzyme reacting with the analyte in a hydrogel and being cured.

According to the present invention, the test strip preferably further comprises an upper cover disposed on the insulation layer.

According to the present invention, preferably the reactive enzyme is a glucose oxidation enzyme.

According to the present invention, preferably the analyte is a blood sugar.

According to a second object of the present invention, there is provided a method of preparing a test strip comprising the steps of:
(a) providing an insulating substrate;
(b) forming an electrode system on the insulating substrate;
(c) forming an insulation layer on the electrode system, which has an accommodation space disposed at one side of the insulation layer; and
(d) providing a gel, disposed in the accommodation space and being cured after dissolving in a reactive enzyme electrochemically reacting with an analyte in a hydrogel, comprising the steps of;
(d1) rolling the gel in a roller;
(d2) laminating the gel on a reaction specimen and die-cutting the gel at a predetermined length; and
(d3) forming a plurality of test strips on the reaction specimen.

According to the present invention, the test strip further comprises an upper cover disposed on the insulation layer.

According to the present invention, preferably the reactive enzyme is a glucose oxidation enzyme.

According to the present invention, preferably the analyte is a blood sugar.

According to the present invention, preferably the hydrogel is provided by a roller.

According to the present invention, preferably the roller is a wind-type film coater device.

According to the present invention, preferably the gel is cured via polymerization by UV light or piezoelectricity method or high pressure oxygen.

Other features and advantages of the present invention and variations thereof will become apparent from the following description, drawings, and claims.

DETAILED DESCRIPTION OF THE INVENTION

The invention is more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

With respect to the drawbacks of the process of the conventional test strip, the present invention provides a method of manufacturing an improved test strip characterized in that a hydrogel comprising a reactive enzyme is coated by a wind-type film coating to replace a well-known drip enzyme solution. The advantages of the method of the present invention are very accurate alignment, a fixed amount of dripping enzyme, an avoidance of drying step and more convenience.

The present invention firstly provides a test strip comprising:

(a) an insulating substrate;

(b) an electrode system disposed on the insulating substrate;

(c) an insulation layer disposed on the electrode system, in which an accommodation space is disposed at one side of the insulation layer for exposing a part of the electrode system to carry out an electrochemical reaction of an analyte; and (d) a gel, disposed in the accommodation space and formed by dissolving a reactive enzyme reacting with the analyte in a hydrogel and being cured and dried.

According to a first preferable embodiment of the present invention, the test strip preferably further comprises an upper cover disposed on the insulation layer.

According to a second preferable embodiment of the present invention, preferably the reactive enzyme is a glucose oxidation enzyme.

According to a third preferable embodiment of the present invention, preferably the analyte is a blood sugar.

According to a second object of the present invention, there is provided a method of preparing a test strip comprising the steps of:

(a) providing an insulating substrate;

(b) forming an electrode system on the insulating substrate;

(c) forming an insulation layer on the electrode system, which has an accommodation space disposed at one side of the insulation layer; and (d) providing a gel, disposed in the accommodation space and being cured after dissolving in a reactive enzyme electrochemically reacting with an analyte in a hydrogel, comprising the steps of;

(d1) providing a roller for rolling the gel;

(d2) laminating the gel on a reaction specimen and die-cutting the gel at a predetermined length; and (d3) forming a plurality of test strips on the reaction specimen.

According to a first preferable embodiment of the present invention, the test strip further comprises an upper cover disposed on the insulation layer.

According to a second preferable embodiment of the present invention, preferably the reactive enzyme is a glucose oxidation enzyme.

According to a third preferable embodiment of the present invention, preferably the analyte is a blood sugar.

According to the present invention, preferably the hydrogel is provided by a roller.

According to the present invention, preferably the roller is a wind-type film coater device.

According to the present invention, preferably the gel is cured via polymerization by UV light or piezoelectricity method or high pressure oxygen.

EXAMPLES

The present invention can be implemented by different ways which are not limited to the following examples hereafter. The following example is an example of the present invention representative of different aspects and features.

Please refer to FIG. 1 which shows a structural view of a test strip of the present invention. The method of preparing a test strip of the present invention comprising the steps of:

(a) providing an insulating substrate 1;

(b) forming an electrode system 2 on the insulating substrate 1;

(c) forming an insulation layer 3 on the electrode system 2, which has an accommodation space 4 disposed at one side of the insulation layer 3; and (d) providing a gel, disposed in the accommodation space and being cured after dissolving in a reactive enzyme electrochemically reacting with an analyte in a hydrogel, comprising the steps of;

(d1) providing a roller 10 for rolling the gel;

(d2) laminating the gel on a reaction specimen 930 and die-cutting the gel at a predetermined length; and (d3) forming a plurality of test strips 940 on the reaction specimen 930. The numeral 950 is a die-cut.

Figure 2A:
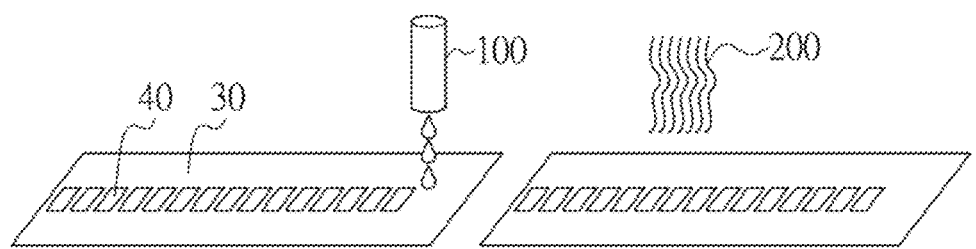
FIG. 2(A) is a schematic view of a conventional process of manufacturing a test strip of prior arts.

The reaction specimen 30 carrying test strips 40 in FIG. 2(A) of prior arts was conveyed to the right side by a first conveyer. The reaction specimen 930 in FIG. 2(B) of the present invention is conveyed to the right side by a second conveyer.

According to a first preferable embodiment of the present invention, the test strip further comprises an upper cover 5 disposed on the insulation layer 3.

Figure 2B:
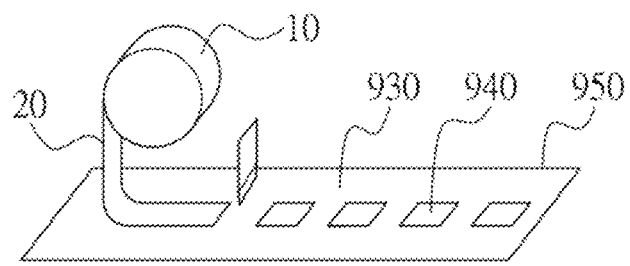
FIG. 2(B) is a schematic view of a process of manufacturing a test strip of the present invention.

Please refer to FIGS. 2(A) and 2(B) which demonstrate comparison between the conventional manufacturing process and the method of the present invention. The present invention provides a method of manufacturing an improved test strip of FIG. 2(B) characterized in that a hydrogel 20 comprising a reactive enzyme is coated by a wind-type film coating to replace a well-known drip enzyme solution 100 of the prior art. The advantages of the method of the present invention of FIG. 2(B) are very accurate alignment, a fixed amount of dripping enzyme, an avoidance of drying step 200 and more convenience. According to the present invention, preferably the hydrogel 20 is provided by a wind-type film coater device (roller) 10. The method of the present invention can produce the test strip in 4-5 seconds while the process of conventional test strips could be produced in 8 minutes.

Those skilled in the art recognize the foregoing outline as a description of a test strip process. The skilled artisan will recognize that these are illustrative only and that many equivalents are possible.

What is claimed is:

1. A method of preparing a test strip comprising the steps of:

(a) providing an insulating substrate;

(b) forming an electrode system on the insulating substrate;

(c) forming an insulation layer on the electrode system, which has an accommodation space disposed at one side of the insulation layer; and (d) providing a gel, disposed in the accommodation space and being cured after dissolving in a reactive enzyme electrochemically reacting with an analyte in a hydrogel, comprising the steps of;

(d1) providing a roller for rolling the gel;

(d2) laminating the gel on a reaction specimen and die-cutting the gel at a predetermined length; and (d3) forming a plurality of test strips on the reaction specimen.

2. The method of claim 1, wherein the test strip further comprises an upper cover disposed on the insulation layer.

3. The method of claim 1, wherein the reactive enzyme is a glucose oxidation enzyme.

4. The method of claim 1, wherein the analyte is a blood sugar.

5. The method of claim 1, wherein the hydrogel is provided by a roller.

6. The method of claim 1, wherein the roller is a wind-type film coater device.

7. The method of claim 1, wherein the gel is cured via polymerization by UV light or piezoelectricity method or high pressure oxygen.

* * * * *